Figure 1:
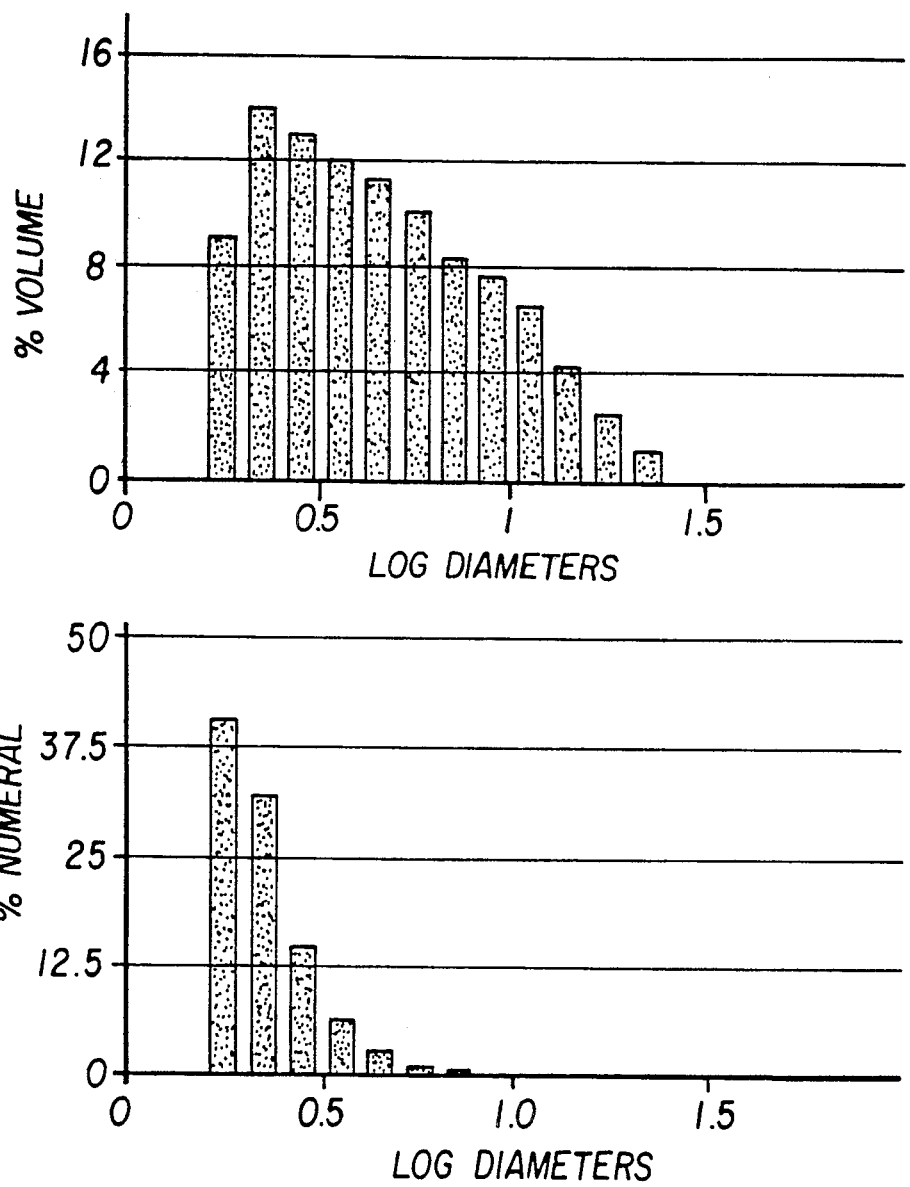

United States Patent [19]

Zagnoli et al.

[11] Patent Number: 5,321,013
[45] Date of Patent: Jun. 14, 1994

[54] PHARMACEUTICAL COMPOSITIONS IN THE FORM OF STABLE SUCRALFATE SUSPENSIONS FREE OF SUSPENDING AGENTS

[75] Inventors: Giorgio G. Z. Zagnoli, Como; Ubaldo Conte, Busto Avsizio; Paolo Colombo; Carla Caramella, both of Pavia, all of Italy

[73] Assignee: Lisapharma SpA, Italy

[21] Appl. No.: 462,950

[22] Filed: Jan. 8, 1990

Related U.S. Application Data

[63] Continuation of Ser. No. 177,451, Apr. 4, 1988, abandoned.

[30] Foreign Application Priority Data

Apr. 15, 1987 [IT] Italy ................................ 20129 A/87

[51] Int. Cl.$^5$ .......................... A61K 31/70; C07H 1/00
[52] U.S. Cl. ...................................... 514/53; 536/4.1; 536/118; 536/121
[58] Field of Search ................... 514/53; 536/4.1, 118, 536/121

[56] References Cited

FOREIGN PATENT DOCUMENTS 0107209  5/1984  European Pat. Off. ............. 514/23
8601406  3/1986  World Int. Prop. O. ............ 514/23

OTHER PUBLICATIONS

R. Nagashima and N. Yoshida, "Sucralfate, a Basic Aluminum Salt of Sucrose Sulfate", Drug Res. 29(II), No. 11 (1979) pp. 1668–1676.

Casillan et al., "Sucralfate suspension for use in treating ulcers", Chemical Abstracts vol. 102 (1985) No. 209472z.

Primary Examiner—Johnnie R. Brown
Assistant Examiner—Elli Peselev
Attorney, Agent, or Firm—Parkhurst, Wendel & Rossi

[57] ABSTRACT

Pharmaceutical compositions in the form of stable sucralfate suspensions free of suspending agents, wherein the sucralfate is present in the form of a gel having self-suspending properties and is suspended in an aqueous carbohydrate solution in a quantity of between 1 and 40% of sucralfate by weight.

Said gel has a surface area exceeding 200 m$^2$/g and is prepared by dissolving powdered sucralfate in an HCl solution and then precipitating it with an NaOH solution added to a pH of between 4 and 4.5.

9 Claims, 2 Drawing Sheets

PHARMACEUTICAL COMPOSITIONS IN THE FORM OF STABLE SUCRALFATE SUSPENSIONS FREE OF SUSPENDING AGENTS

This is a continuation of application Ser. No. 07/177,451 filed Apr. 4, 1988, now abandoned.

This invention relates to pharmaceutical compositions in the form of stable suspensions containing sucralfate as active principle and free of suspending agents.

Sucralfate is basic aluminium saccharose sulphate and is used in human medicine for treating gastric and duodenal ulcers. It acts in the digestive tract by covering the mucous membrane of the stomach and duodenum by the formation of polyvalent bonds with the ulcerated mucous membrane parts. In this manner an effective protection is obtained for the injured mucous membrane part, together with a generally better protection of the mucous membrane against the administration of gastrolesive medicaments such as non-steroid anti-inflammatories.

Compositions containing sucralfate are generally prepared as solid pharmaceutical forms such as tablets, granulates or powders. These pharmaceutical forms have the drawback that the active principle presents only a reduced surface area which limits its mucous membrane protection function.

On the basis of these considerations an improvement would be obtained by using liquid preparations in suspension form which would allow a more rapid and complete lining of the mucous membrane and thus ensure greater therapeutic effectiveness.

In preparing pharmaceutical suspensions, suspending agents are normally used to reduce the sedimentation rate of the suspended particles and, should sedimentation occur with time, to allow complete resuspension of the solid particles by simple shaking.

In aqueous suspension, the mentioned properties can be obtained by adding glycerin, glucose or saccharose syrup, sorbitol solution or substances which increase the density of the suspending medium, or by adding thickeners or viscosity-raising agents. Substances able to increase viscosity and prevent sedimentation of solid particles are generally cellulose or gum derivatives. All attempts to produce pharmaceutical compositions containing sucralfate in suspension by means of substances normally used in the pharmaceutical field for producing stable suspension have failed.

DE patent 3430809 describes a method for stabilising pharmaceutical preparations in the form of suspension containing sucralfate. In this method, 1-5% of gum xanthan and 1-12.5% of a peptizer with respect to the sucralfate content are added as suspending agents. Stable sucralfate suspensions are obtained in this manner, but with the drawbacks of the cost of the added substances, the operations required to form the suspending medium and the need to micronize the raw material.

We have now found that it is possible to obtain stable sucralfate suspensions without adding suspending agents, by using sucralfate with particular physico-chemical properties. In this respect, we have found that sucralfate with suitable physico-chemical characteristics acts as a thickening and suspending agent and therefore enables stable suspensions to be prepared without the use of any additive belonging to the suspending and viscosity-raising agent class, such as gum xanthan, cellulose derivatives or other gums or peptizers.

This physico-chemical form also dispenses with the need to micronize the active principle as the product has a particle diameter less than 10 microns. When tested on man, the product obtained has proved perfectly tolerated, and on endoscopic examination has been shown to produce regression of pyrosis and epigastralgia, and improvement in reflux esophagitis and gastroduodenal erosion.

Consequently, the present invention firstly relates to the preparation of sucralfate in a physico-chemical form known as wet gel, for use in preparing stable suspensions without the use of suspending and viscosity-raising agents.

The invention also relates to the method for preparing stable sucralfate suspensions and the compositions obtained.

The wet gel sucralfate according to the present invention is prepared from powdered sucralfate by treatment with an HCl solution at a concentration of between 3.7% and 37% while stirring at ambient temperature.

The solution obtained is treated at ambient temperature with an NaOH solution at a concentration of between 3.7% and 37% until a pH of between 4.0 and 4.5 is obtained.

The precipitated gel is recovered by centrifuging and is washed by dispersion and agitation in water followed by centrifuging, this operation being repeated several times.

Preservatives such as sorbic acid and sodium benzoate in a quantity of 0.5-2 per mille by weight are added to the gel prepared in this manner, which is then preserved in the wet state until used for preparing the suspension.

The sucralfate wet gel suspension which is an object of the present invention, shows the characteristic property of adhesion to mucous membranes; this property can easily be appreciated by tasting the product.

In fact when tasting a few milliliters of the suspension one clearly notices an astringent binding sensation at the buccal mucous membranes; this sensation is accompanied by an evident whitening of the tongue and a persistent adhesion of the product to the buccal mucous membranes.

Sucralfate in powder form, which does not possess the physical structure discussed above, does not present this characteristic. In fact, a suspension prepared starting from commercial Sucralfate in powder form (produced by Formion) does not manifest on tasting it the sensation described for our product.

The prepared wet gel has the following weight composition:

| Saccharose sulphate | 9–31% |
|---|---|
| Aluminium | 4–14% |
| $H_2O$ | 30–80% |

Granulometric Characteristics of the Dispersed Phase (Coulter Counter TAII, Capillary Orifice 70µ) FIG. 1

Examined dimensional range: 1.3–40µ volume-surface diameter: 3–4µ (less than 6µ)

Percent/by weight of solids below 5µ: not less than 50%

Figure 2:
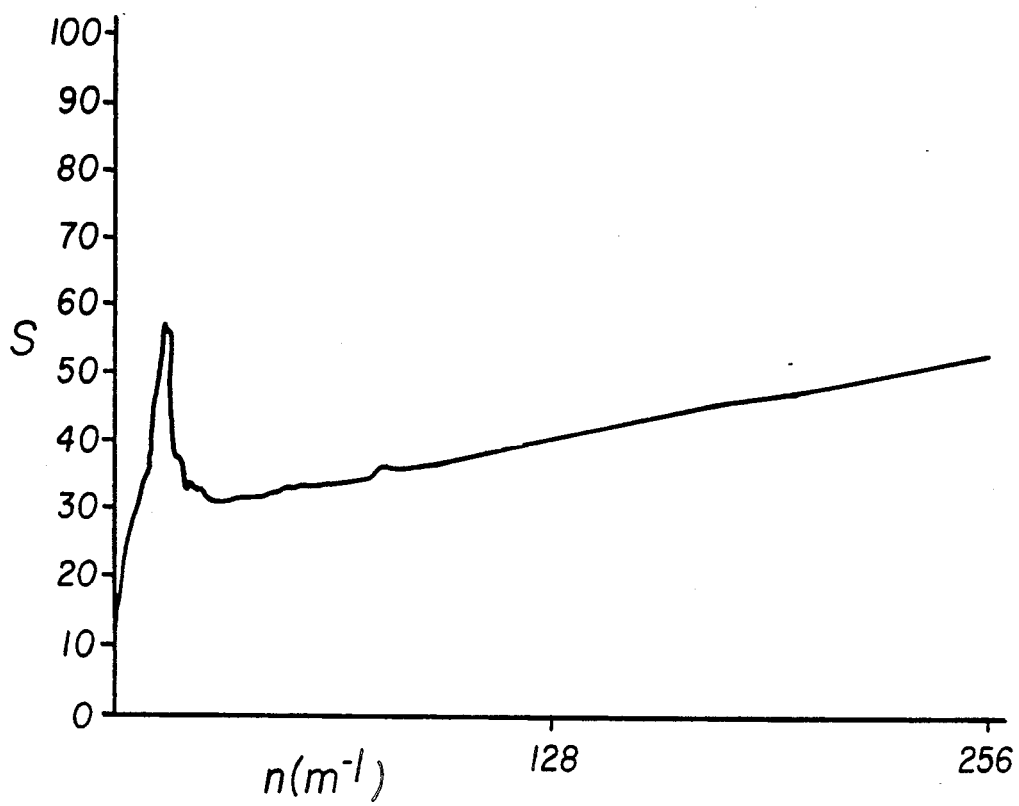

Rheological Characteristics (Rotovisco RV 12; Measurement Systems NV and MVI, Temperature 25° C.) FIG. 2

The aqueous suspensions present, even after agitation for the sampling, a significant creep limit, both static and dynamic, comprised between 50 and 100 (typically for a 20% wt/vl suspension at 25° C.).

The limit viscosity (calculated from the linear portion of the rheogram) is of 10-30 mPa.s.

After rheological standing the suspensions show an increase of the initial creep limit (presence of a spur) followed by a rapid fall due to breaking of the thixotropic structure.

A 20% wt/vl commercial suspension Ulcogant, on the contrary, differs as follows from a similar sucralfate gel suspension:

Granulometric Characteristics volume-surface diameter: 7-8 m$\mu$
Percent (by weight) of solids below 5 m$\mu$: less than 20%

Figure 3:
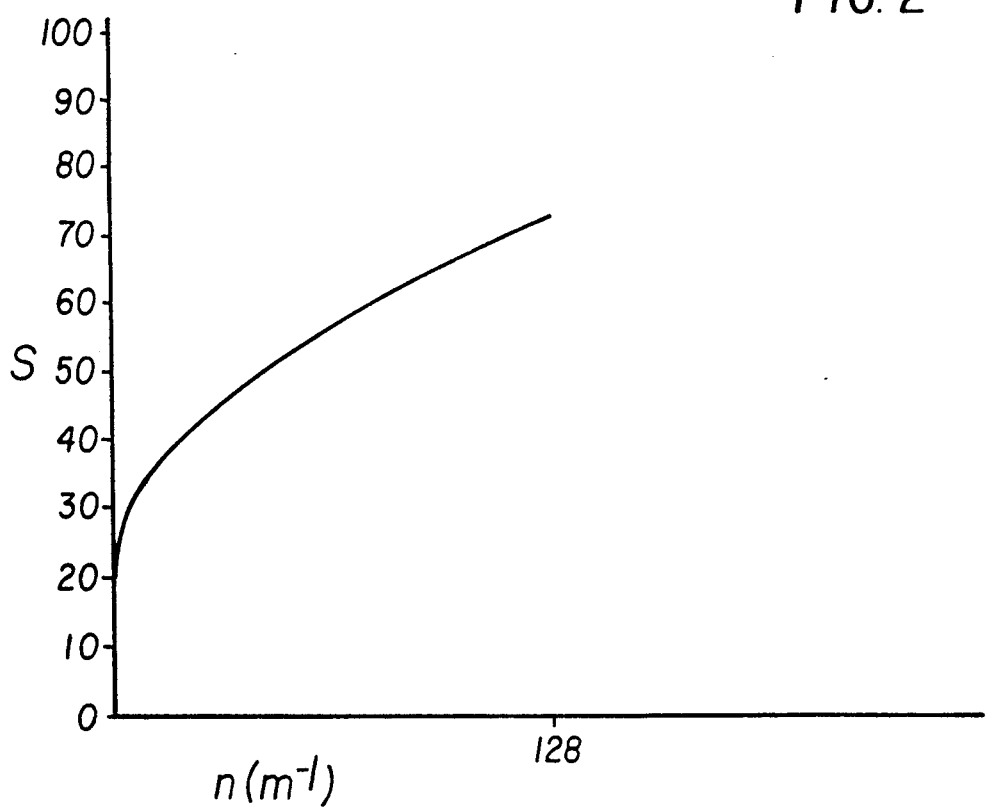

Rheological Characteristics (FIG. 3)

Static and dynamic creep limit below 20 Pa
limit viscosity: about 25 mPa.s
after rheological standing no significant increase of the initial creep limit is shown.

In addition to the described method, the wet sucralfate gel can be prepared from saccharose octasulphate or one of its synthesis precursors.

Pharmaceutical compositions containing sucralfate in suspended form are prepared by dispersing said wet sucralfate gel in a carbohydrate solution at ambient temperature, homogenizing by means of a turbine, and then filtering the suspension through a 30-200 mesh screen.

Alternatively, pharmaceutical compositions containing sucralfate in suspended form according to the present invention can be prepared by preparing the sucralfate in gel form directly in the suspension, starting from the powdered sucralfate.

The carbohydrate solution is preferably a sorbitol solution at a concentration of 5-40% by weight. This solution contains small quantities of preservative such as 0.05-0.5% of sorbic acid or sodium benzoate and small quantities of flavourings such as 0.05-0.5% of mint essence.

The pharmaceutical composition contains 1-40% by weight of sucralfate in suspension in the form of gel having self-suspending characteristics.

Said composition, when containing 20% by weight of sucralfate, has a thixotropic rheological behaviour (Rotovisko, measure system PK.1) with a shear limit of between 300 and 450 Pa, a thixotropy area of between $30 \times 10^4$ and $50 \times 10^4$ Pa.s$^{-1}$ and a viscosity after rupture of the thixotropic structure of between 30 and 50 mPa.s. The dispersed particles have a mean volume-surface diameter of less than 6 microns.

This composition retains its suspension characteristics for some hundreds of days, is thixotropically structured and becomes fluid on agitation.

The fact that stable sucralfate suspensions are obtained according to the present invention is attributable to the particular gel form of the sucralfate, which allows the final suspension to become thixotropically organized. This suspension after a suitable standing time is perfectly homogeneous, stable and consistent, the thixotropic structure acquired while the preparation is standing enabling these properties to be permanently maintained.

Normal shaking, as applied to common pharmaceutical suspensions, returns the sucralfate suspension to sufficient fluidity to enable it to be easily poured, so that the prescribed dose of product can be withdrawn without problem.

In the following laboratory tests the therapeutic activity of the sucralfate suspension from gel according to the invention is reported in comparison with the activity of sucralfate suspensions according to the prior art.

TESTS IN VIVO ON RATS

Test No. 1

In order to study the mechanisms of gastric citoprotection and to quantitively evaluate the protective effect of wet sucralfate gel, we have carried out an experiment on approximately 200 female albino rats (Wistar type strain wt. 250-300 g).

In particular, we intended to verify the protection and/or prevention ability of sucralfate gel vis-a-vis the insurgence of gastric ulcers induced by multiple and combined stresses, using the Caradente method (Proc.XII Int. Cong. Int. Chronobiol. Il Ponte pag. 156-177, 1977) and comparing it with sucralfate powder of prior art.

The rats were fed, 48 hours ahead of the experiment, with a sucrose 17% solution in order to facilitate the evacuation from the stomach of raw fibres which are normally present in the diet.

The animals were then provided through probe intragastrically, with 0.3 ml/100 g body weight of a sucralfate suspension, anaesthetized with ethyl ether vapor and placed in narrow contention cages, which were then maintained in a cold environment at 6° C. for 4 hours. The controls were probed with an equal volume of physiological solution and handled in the same way.

The rats were sacrified and their stomachs were placed in physiological solution, split at the level of the great curve and flattened with the aid of pins on a cork surface.

The formed ulcers were read in mm using a dissection microscope WILD M 650 (Heerbrugg Leitz Italia, Milan) with $\times 16$ objective and micrometric scale ocular, in a double blind control.

Experiment No. 1

30 rats were used, divided in 3 groups:
1—Control Group
2—Group previously treated with sucralfate powder (commercial product in 10% wt/vol suspension)
3—Group, previously treated with wet sucralfate gel in 10% wt/vol suspension The rats were then stressed with the previously mentioned method; the evaluation of the effect is reported in the table.

TABLE 1

| | Ulcers induced by stress (in mm ± ASD*) | |
|---|---|---|
| Controls | Sucralfate Powder 10% suspension | Sucralfate Wet gel 10% suspension |
| 27.78 (±9.82) | 12.23 (±5.53) | 4.24 (±1.54) |

*ASD = average standard deviation

Experiment No. 2

The gastroprotective activity of sucralfate gel administered in two different concentrations, 10% and 20% in comparison with a ready made sucralfate 20% suspension commercially available in Germany (Merck Ulcogant, Lot. n. 3.530) was tested.

To the three groups the same volume suspension was administered for the three preparations mentioned.

On group was obviously used as control.

The experimental results are reported in Table 2.

TABLE 2

| | Ulcers induced by stress (in mm ± ASD) | | |
|---|---|---|---|
| Control | Ulcogant 20% suspension | Sucralfate Wet gel 20% suspension | Sucralfate Wet gel 10% suspension |
| 59.5 (±12.73) | 7.69 (±1.94) | 8.29 (±1.95) | 7.56 (±2.07) |

Experiment No. 3

40 albino Wistar strain female rats were utilized, divided in 2 groups.

To the 1st group the Ulcogant suspension diluted to 10% with water was administered, and to the 2nd the wet gel sucralfate 10% suspension.

The results obtained, after stress, in the identical conditions reported for experiment 2, were:

TABLE 3

| | Ulcers induced by stress (in mm ± ASD) | |
|---|---|---|
| Control | Ulcogant suspension diluted to 10% | Sucralfate Wet gel 10% suspension |
| 59.5 (±12.73) | 14.77 (±5.31) | 6.15 (±1.36) |

Conclusions

The above results evidently show that the gastroprotective activity of 10% by w. sucralfate wet gel is high and equivalent to the one that can be obtained by administration of the same amount of a commercial suspension having 20% by w. concentration of sucralfate.

A method of preparing the wet thixotropic sucralfate gel and the relative stable suspension for pharmaceutical use are described hereinafter by way of non-limiting examples.

EXAMPLE 1

Preparation of the wet sucralfate gel:

50 g of powdered sucralfate are suspended in 800 ml of 1N HCl and the suspension stirred until completely dissolved. The solution obtained is filtered and 1N NaOH added to pH 4-4.5, to precipitate the sucralfate in the form of gel.

The gel is centrifuged and the supernatant liquid is removed. 250 ml of $H_2O$ are added, the mixture stirred, centrifuged and the supernatant removed.

This operation is repeated three times.

0.1% by w. of ascorbic acid and sodium benzoate are added to this gel, which is then stored in its wet state until the moment of its suspension. The gel can be filtered under a pressure of 1 atm or can be pressed to reduce the percentage of water.

The gel thus prepared has the following characteristics: content:

| | |
|---|---|
| saccharose sulphate | 9-13% |
| aluminium | 4-14% |
| $H_2O$ | 30-80% | chemical structure:
  a) IR spectrum (see FIG. 1)
  b) X-ray: amorphous product
size distribution:
  dvs about 6 microns
  range 2-30 microns
rheology: (10% suspension in water) Rotovisco-Haake, RV 12, PKI system, thixotropic behaviour:

| | |
|---|---|
| shear limit | 250-500 Pa |
| thixotropy area | 10-35 × $10^4$ $Pa.s^{-1}$ |
| limiting viscosity | 10-15 mPa.sec |

EXAMPLE 2

Preparation of sucralfate suspension:
The following substances are used:

| | |
|---|---|
| sucralfate gel | 20 g |
| 70% sorbitol | 50 ml |
| sorbic acid | 0.1% |
| sodium benzoate | 0.1% |
| mint essence | 0.1% |
| purified $H_2O$ to make up to | 100 ml |

The sucralfate is dispersed in the mixture of 70% sorbitol, sorbic acid, sodium benzoate and mint essence. The dispersion is homogenized with a turbine and filtered through a 200 mesh screen.

The suspension obtained has the following properties:

| | |
|---|---|
| shear limit (20° C.) | 400 Pa |
| thixotropy area | 35 × $10^4$ $Pa.s^{-1}$ |
| limiting viscosity | 40 mPa.s |
| density (20° C.) | 11.15 $g.cm^{-1}$ |
| pH | 4.9 |

After storing for 180 days in a graduated stoppered cylinder (diameter 25 mm) the suspension shows no supernatant layer and appears thixotropically structured.

On shaking, it becomes fluid with no permanent sediment.

We claim:

1. A process for preparing a pharmaceutical composition consisting essentially of a stable suspension of sucralfate, free of suspending agents, wherein the suspended sucralfate particles have a volume/surface diameter of less than 6 microns, comprising the steps of:
   dissolving commercial grade powder form sucralfate in aqueous HCl solution;
   adding NaOH to the solution until the solution has a pH in the range of 4.0 to 4.5 to produce a sucralfate gel;
   washing the sucralfate gel with water;
   recovering the washed sucralfate gel by decantation to obtain a sucralfate gel having about 30 to 80% by weight water; and
   dispersing and homogenizing the wet recovered sucralfate gel in an aqueous solution of 5 to 40 weight percent sorbitol wherein the sucralfate gel is used in an amount such that the resultant aqueous suspension contains 1 to 40% by weight of sucralfate.

2. The process of claim 1, wherein said HCl solution has a concentration of between 3 and 37%.

3. The process of claim 1, wherein said NaOH solution has a concentration of between 3 and 37%.

4. The process of claim 1, wherein said wet sucralfate gel is washed several times by agitation in water and then is recovered by centrifuging.

5. The process of claim 1, wherein said dispersing and homogenizing of the wet recovered sucralfate gel in aqueous solution of sorbitol is carried out by means of a turbine.

6. The process of claim 1, wherein said sorbitol solution contains small quantities of preservatives and flavorings.

7. The process of claim 1, conducted at ambient temperature.

8. A pharmaceutical composition consisting essentially of a suspension of 1 to 40 weight percent sucralfate in an aqueous solution of 5 to 40 weight percent sorbitol, wherein the suspended sucralfate particles have a volume/surface diameter of less than 6 microns, such composition being free of suspending agent.

9. The pharmaceutical composition of claim 8, wherein the sorbitol concentration is in the range of 10 to 40 weight percent.

* * * * *